United States Patent [19]
Schmitz et al.

[11] Patent Number: 6,050,724
[45] Date of Patent: Apr. 18, 2000

[54] METHOD OF AND DEVICE FOR POSITION DETECTION IN X-RAY IMAGING

[75] Inventors: Georg Schmitz; Jörg Sabczynski, both of Norderstedt, Germany

[73] Assignee: U. S. Philips Corporation, New York, N.Y.

[21] Appl. No.: 09/014,714

[22] Filed: Jan. 28, 1998

[30] Foreign Application Priority Data

Jan. 31, 1997 [DE] Germany .......................... 197 03 556

[51] Int. Cl.[7] ...................................... A61B 6/00
[52] U.S. Cl. ............................. 378/205; 378/62
[58] Field of Search ............... 378/62, 205, 206

[56] References Cited

U.S. PATENT DOCUMENTS

| | | | |
|---|---|---|---|
| 5,097,839 | 3/1992 | Allen | 378/901 X |
| 5,588,430 | 12/1996 | Bova et al. | 378/205 X |
| 5,772,594 | 6/1998 | Barrick | 378/205 X |
| 5,923,727 | 1/1999 | Navab | 278/207 |
| 5,954,647 | 9/1999 | Bova et al. | 378/205 |

FOREIGN PATENT DOCUMENTS

WO9740763  6/1997  WIPO .

*Primary Examiner*—David P. Porta
*Assistant Examiner*—Drew A. Dunn
*Attorney, Agent, or Firm*—Dwight H. Renfrew

[57] ABSTRACT

The invention relates to a method of position detection in X-ray imaging, and to a device for carrying out such a method by means of an X-ray apparatus, a detector device, including at least two detector elements, and an indicator device. The exact association of the X-ray image with the object imaged is very important notably for intraoperative imaging. Exact knowledge of the position and orientation of the components of the X-ray apparatus associated with the imaging system is required for this purpose. However, it is often problematic that the lines of sight of the position measuring system are obscured by attending staff or other apparatus. Therefore, in the device according to the invention the detector device is mounted on the X-ray apparatus and the indicator device is provided so as to be stationary on the object to be examined or stationary relative to the object to be examined. Also described is a method of position detection in X-ray imaging by means of such a device.

20 Claims, 3 Drawing Sheets

METHOD OF AND DEVICE FOR POSITION DETECTION IN X-RAY IMAGING

BACKGROUND OF THE INVENTION

1. Field of the Invention

The invention relates to a method of position detection in X-ray imaging as well as to a device for carrying out such a method which includes an X-ray apparatus, a detector device, comprising at least two detector elements, and an indicator device.

2. Description of Related Art

A device for position detection in medical imaging is described in WO 97/40763. Therein, two cameras which are capable of detecting visible light or infrared light are connected to a stand so as to be stationary in space. Diodes which emit light that can be detected by the cameras are attached to a treatment instrument. The position of the treatment instrument in a co-ordinate system which is coupled to the cameras can be determined by means of the cameras. This position can be converted into an image position by means of a predetermined transformation matrix, the image having been formed in advance by means of computer tomography (CT) or magnetic resonance (MR) tomography. In order to determine said transformation matrix for converting camera coordinates into image co-ordinates, markers are provided on the patient during the image acquisition; these markers are also reproduced so that they are visible in the image. The treatment instrument provided with diodes, or a separate indicator instrument provided with diodes, is subsequently moved to these markers so that the position thereof is determined in camera co-ordinates. This establishes the necessary link between camera co-ordinates and image co-ordinates and enables the position of the treatment instrument to be reproduced in the image during a treatment.

The exact association of a point in an X-ray image with a point in or on an object to be examined may also be very important in conventional X-ray imaging, notably in the case of intra-operative imaging. The exact determination of the position of a treatment instrument or another medical apparatus, for example a radiation therapy apparatus, is also desirable. According to the known method it is necessary to provide the object to be examined with markers in fixed positions for a prolonged period of time, i.e. already upon the image acquisition by means of CT or MR and later upon the position detection by means of the cameras. The mounting of the cameras on a stationary stand is not ideal either for position detection during X-ray imaging. It is notably in the case of intra-operative X-ray imaging by means of a pivotable X-ray apparatus that the lines of sight of the camera are often obscured by the X-ray apparatus itself or by the attending staff when the cameras are mounted in this manner.

SUMMARY OF THE INVENTION

Therefore, it is an object of the invention to provide a suitable method of position detection for X-ray imaging as well as a device for carrying out such a method.

In respect of the method this object is achieved according to the invention in that at least one X-ray image of an object to be examined is formed by means of an X-ray apparatus and the position of an indicator device, provided so as to be stationary on the object to be examined or stationary relative to the object to be examined, in a detector co-ordinate system coupled to the detector device is determined by means of a detector device mounted on the X-ray apparatus, the position of the X-ray apparatus is determined in an object co-ordinate system which is coupled to the object to be examined, and subsequently the position of an object point which is imaged as an image point in an X-ray image is determined in the object co-ordinate system.

The position of the indicator device is detected in the same position of the X-ray apparatus as that in which the X-ray image was formed. Therefore, these two operations can also be performed simultaneously. The detection of the position of the indicator device in the detector co-ordinate system automatically yields the position of the detector device in the object co-ordinate system since the indicator device is arranged to be stationary relative to the object to be examined and the object co-ordinate system is rigidly coupled to the object to be examined and hence also rigidly to the indicator device. This automatic extraction of the position of the indicator device in object co-ordinates from the position detected in detector co-ordinates is given by the functionality of the position measuring system formed by the detector device and the indicator device.

Because the detector device is mounted so as to be stationary on the X-ray apparatus, the position of the X-ray apparatus in the object co-ordinate system can be readily determined from the position of the detector device in the object co-ordinate system which is thus known. Preferably, characteristic points, such as the position of the focal point and the position of the imaging plane, are determined during the determination of the position of the X-ray apparatus. Subsequently, on the basis thereof a pixel in an X-ray image can be associated with an object point of the object in the object co-ordinate system. In as far as only a single X-ray image was formed, the position of an object point associated with an image point can be determined only in as far as an image point can be associated with a ray situated between the focal point and the imaging plane of the X-ray apparatus. It is only when a plurality of X-ray images are formed from different positions of the X-ray apparatus that more accurate determination of the position of the object point is possible.

In a version of the invention at least two X-ray images of the object to be examined are formed from different directions, the position of the focal point and the position of the imaging plane of the X-ray apparatus in the object co-ordinate system being determined simultaneously with the X-ray image acquisition. The position of an object point, being reproduced as an image point in both X-ray images, can be exactly determined in the object co-ordinate system already in the case of two X-ray images. For example, for this purpose it suffices to use two X-ray images which have been acquired from two mutually perpendicular directions.

In a further version of this method, the position of the object point is determined by means of two straight lines, the first straight line extending through the image point associated with the object point in a first X-ray image and through the first position of the focal point, whereas the second straight line extends through the image point associated with the object point in a second X-ray image and through the second position of the focal point, the object point being the point of intersection of the two straight lines or the central point of the shortest connecting line between the two straight lines. The object point can thus be very accurately determined by a simple calculation of the point of intersection of two lines or by a calculation of a point which is situated at the center of the shortest connecting line between the straight lines.

In a further version of the method according to the invention, the detector device detects the position of a medical apparatus, provided with a further indicator device, in the detector co-ordinate system, the position of the medical apparatus in the image coordinate system of an X-ray image being determined from its position in the detector coordinate system. Using the rule for conversion between detector co-ordinates and object coordinates, already determined at the beginning, first the position of the medical apparatus in the object co-ordinate system can be determined from the detected position of the medical apparatus in the detector co-ordinate system, and subsequently its position in the image coordinate system of an X-ray image can be determined on the basis thereof. This enables reproduction of the position of the medical apparatus, for example being a treatment instrument, directly in the X-ray image so that the operator always knows in which position on or in the object to be examined the instrument is situated, even when parts of the instrument are not visible from the outside. The medical apparatus may also be, for example a radiation therapy apparatus whose position in the image co-ordinate system can be exactly determined by means of the method according to the invention, thus enabling the therapy beam to be aimed exactly at the area to be treated.

In a further version of the method according to the invention which is based thereon, the position of the medical apparatus in the image co-ordinate system is calculated from the point of intersection between the imaging plane and a straight line which extends through the focal point and the position of the medical apparatus in the object coordinate system. Because the position of the X-ray apparatus, notably the position of the focal point and the imaging plane of the X-ray apparatus, and the position of the medical apparatus in the object co-ordinate system are determined during the formation of an X-ray image, the position of the medical apparatus in the image co-ordinate system can be determined by simple determinations of the point of intersection of a straight line with the imaging plane.

The object in respect of a device for carrying out the method according to the invention is achieved by means of a device of the kind set forth which is characterized in that the detector device is mounted on the X-ray apparatus and that the indicator device is provided so as to be stationary on the object to be examined or stationary relative to the object to be examined. It is thus achieved that the field of view of the detector device and the exposure field of the X-ray apparatus correspond mainly or at least substantially. In the known device, in which the detector device is mounted on a stand, the field of view of the detector device could be obscured by an operator or an apparatus, thus preventing the determination of the position of an object point or a surgical instrument when an optical detector device is used; this nuisance can hardly occur in the device according to the invention. During an X-ray exposure, the exposure field will in all cases be free from surgical instruments or attendants, so that the position of the indicator device mounted on the object to be examined can be detected at the same time by means of the detector device. Generally speaking, the area between the X-ray apparatus and the object to be examined is also free from other apparatus and attending staff during periods in which no X-ray exposures take place, so that during these periods the position of treatment instruments in the detector co-ordinate system can also be detected by the detector device and subsequently determined in the image co-ordinate system.

The detector device in a further embodiment of the device according to the invention is mounted on the X-ray source or on the X-ray image pick-up or X-ray image intensifier device. The risk that lines of sight of the detector device are obscured is very small when the detector device is mounted in this manner. In choosing the position of the detector device, of course, it must be ensured that the lines of sight of the detector device are not obscured by parts of the X-ray apparatus itself, for example the patient table, in given positions of the X-ray apparatus. Therefore, the detector device is preferably mounted on a part of the X-ray apparatus which is situated above the object to be examined in most positions of the X-ray apparatus.

In a further embodiment of the invention, a further indicator device is mounted on a medical apparatus, notably a treatment instrument or a radiation therapy device. The detection of the position of the medical apparatus can take place simultaneously with the formation of an X-ray image, but also at any other instant. A condition in this respect, however, is that the instantaneous position of the X-ray apparatus was also detected and determined by means of the detector device, because this position data is required for determining the position of the medical apparatus in the image co-ordinate system.

According to the invention, the indicator devices preferably include optical light source markers, for example light emitting diodes which emit infrared light or visible light, retro-reflective markers or markers provided with a recognition pattern. Corresponding optical detectors, which are sensitive to the relevant radiation, are used for the detector device. When retro-reflective markers are used, moreover, in the vicinity of the detector device there is arranged a further radiation source, whose radiation is reflected by the markers and subsequently detected by the detector device, so that the position of the markers can be determined. When markers provided with recognition patterns are used, the detector device includes appropriate detectors which are capable of determining a position on the basis of the recognition of such patterns.

Moreover, the detector device in a further embodiment of the device according to the invention includes two optical detectors, detecting a respective two-dimensional position, or three optical detectors, each of which detects a respective one-dimensional position, said detectors being capable of detecting infrared light or visible light and preferably being infrared CCD cameras, each of the indicator devices including at least three light emitting diodes emitting infrared light or visible light. This represents a simple and inexpensive solution enabling detection of positions with a high accuracy.

The indicator device in an alternative embodiment of the device according to the invention includes at least one electromagnetic transmitter device, the detector device including at least one electromagnetic receiver device. The electromagnetic transmitter device, being capable of generating mutually perpendicular electromagnetic fields, and the electromagnetic receiver device, being capable of detecting electromagnetic fields, can be used instead of the optical indicator and detector device. The problem of obscuring of lines of sights by attendants or apparatus is not very significant when electromagnetic devices are used, for example small coil systems; however, the radius of action of the optical indicator and detector device is greater.

The X-ray apparatus in a preferred embodiment of the invention is a C-arm X-ray apparatus. An X-ray apparatus of this kind is often used for intra-operative X-ray imaging in order to form X-ray images of the patient from different positions during the operation. Because the detector device is rigidly mounted on the X-ray apparatus, the position of the detector device changes directly during a rotation of the C-arm, whereas the position of the indicator device on the patient is stationary or stationary relative to the patient. Therefore, the co-ordinate system of the indicator device (the object co-ordinate system) is used as a fixed reference co-ordinate system.

BRIEF DESCRIPTION OF THE DRAWINGS

The invention will be described in detail hereinafter with reference to the drawing. Therein.

DETAILED DESCRIPTION OF THE PREFERRED ENBODIMENTS

Figure 1:
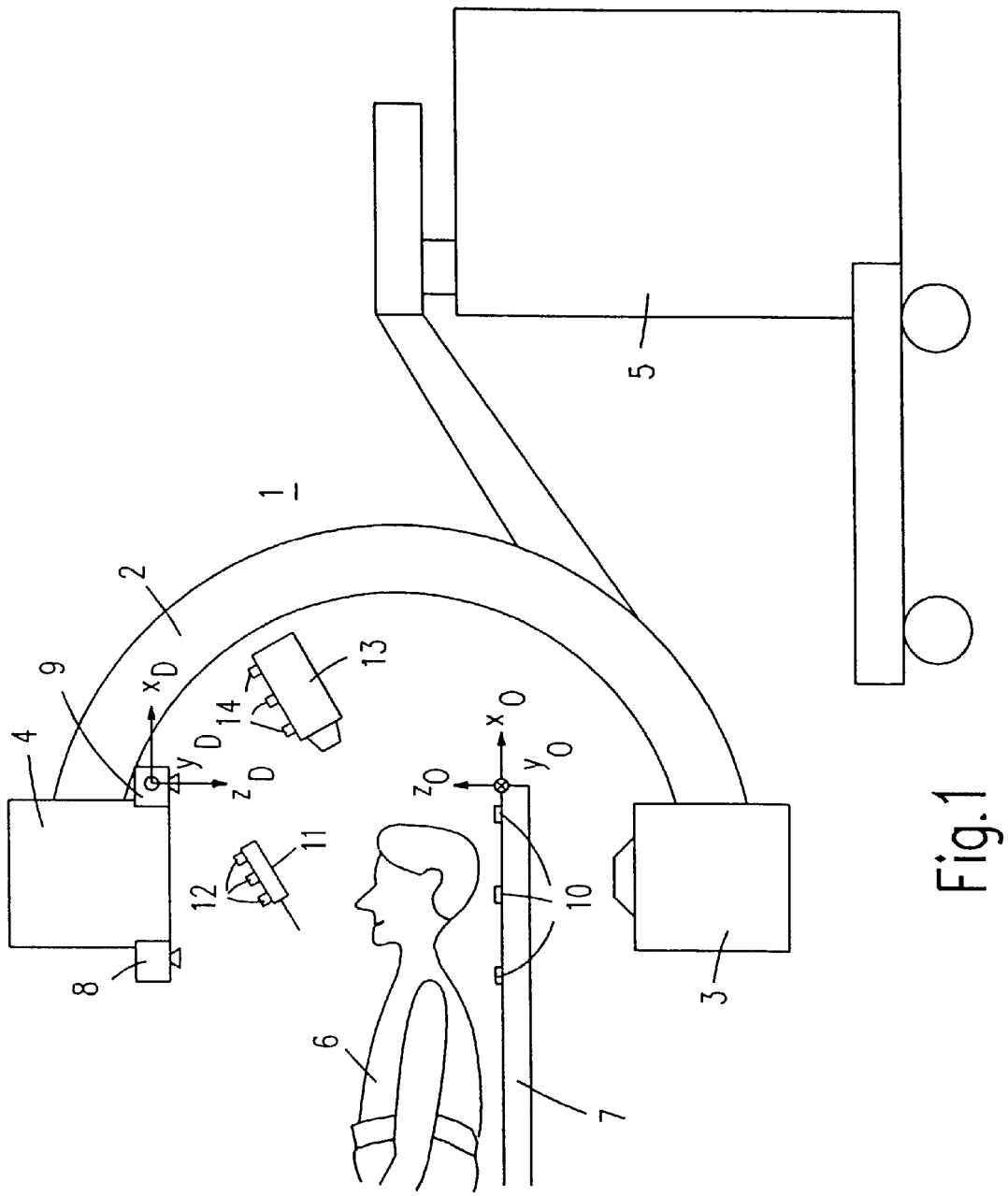
FIG. 1 shows diagrammatically a device according to the invention which includes a C-arm X-ray apparatus.

FIG. 1 shows a device according to the invention which includes a C-arm X-ray apparatus 1. At the lower end of the C-arm 2 there is mounted an X-ray source 3 whereas an image pick-up and intensifier device 4 is mounted at the upper end of the C-arm 2. The electronic circuitry for control and data processing of the X-ray apparatus is accommodated in the control and processing unit 5. The patient 6 to be examined is arranged on a patient table 7 in such a manner that an X-ray image of the head of the patient can be formed. Two infrared CCD cameras 8, 9, constituting the detector device, are mounted to the sides of the image pick-up device 4. The cameras 8, 9 are mounted in such a manner that their field of view corresponds essentially to the exposure field of the X-ray apparatus 1, i.e. the area irradiated by the X-ray source 3. Consequently, the cameras 8, 9 can detect infrared light signals emitted by three infrared light emitting diodes mounted on the patient table. The light emitting diodes 10 are mounted on the patient table in such a manner that they are not obscured by the head of the patient 6. Furthermore, by way of example, a treatment instrument 11 is shown in the irradiation zone; three infrared light emitting diodes 12 are also mounted on this instrument. Furthermore, a radiation therapy apparatus 13 is shown as an example of a further medical apparatus, said apparatus 13 also including three infrared light emitting diodes 14. Even though this apparatus is not situated in the exposure field of the X-ray apparatus 1, the field of view of the cameras 8, 9 is so large that signals from the light emitting diodes 14 can also be detected when the radiation therapy apparatus 13 is not situated too far from the patient 6.

The three infrared light emitting diodes 10 on the patient table form an indicator device. Similarly, the three light emitting diodes 12 on the instrument 11 and the three light emitting diodes 14 on the radiation therapy apparatus also form a respective indicator device. Each of the two cameras 8, 9 is capable of detecting the two-dimensional position of a light emitting diode. The three-dimensional position of a light emitting diode can be determined from the signals from a light emitting diode which are detected by the two cameras 8, 9. In order to determine the position of an apparatus, for example the patient table 7, in three-dimensional co-ordinates, three light emitting diodes are required as shown for each indicator device.

The positions are first determined in the detector co-ordinate system D which is formed by the co-ordinate axes $X_D, Y_D, Z_D$. The detector co-ordinate system D is rigidly coupled to the detector device, i.e. to the camera 9 in the embodiment shown. Because of the functionality of the position measuring system consisting of the cameras 8, 9 and the light emitting diodes 10, 12, 14, positions determined in the detector co-ordinate system D can also be readily converted into object co-ordinates of an object co-ordinate system O. The object co-ordinate system O, formed by the co-ordinate axes $x_o, y_o, z_o$, is rigidly coupled to the object to be examined, in this case the patient 6, or rigidly to the patient table 7 which is immobile relative to the patient 6. The position measuring system thus enables the detection of the three-dimensional position of an apparatus, comprising an indicator device, in the detector co-ordinate system D and the conversion of this position into object co-ordinates of the object co-ordinate system O.

The method of determining the position of an object point, imaged as an image point in at least one X-ray image, in the object co-ordinate system O will be described in detail hereinafter on the basis of the flow chart shown in FIG. 2. First of all, in block 101 a first X-ray image is formed in a first position of the C-arm. At the same time the cameras 8, 9 detect the position of the light emitting diodes 10 in detector co-ordinates. The position of the light emitting diodes 10 at the same time yields the position of the patient table 7 and the position of the object co-ordinate system O (or the position of the origin of the object coordinate system O).

Subsequently, in block 102 the position of the cameras 8, 9 is determined in object co-ordinates; this is simply possible because of the functionality of the position measuring system and because the position of the object co-ordinate system O in detector coordinates is known.

Subsequently, in block 103 the position of the X-ray apparatus 1 in the object co-ordinate system I is determined. The focal point in the X-ray source 3 and the imaging plane in the image pick-up device 4 are chosen as characteristic points of the X-ray apparatus 1, their positions being determined in object co-ordinates. To this end, the positions of the focal point and the imaging plane are converted from detector co-ordinates into object co-ordinates. The positions in detector co-ordinates are assumed to be known for the execution of the method according to the invention and are obtained, for example by means of an calibration operation which is to be performed once for the X-ray apparatus 1 while using a calibration phantom; this will be described in detail hereinafter.

In block 104 a straight line is plotted through the focal point and the image point in the imaging plane for which the associated object point is to be determined in the object co-ordinate system. The object point searched is situated on this straight line.

More accurate determination is not possible if only one X-ray image is used. If the position of the object point in the object co-ordinate system is to be determined exactly, a second X-ray image will be required which must be formed in a position of the C-arm which deviates from that in which the first X-ray image is formed. The steps of the blocks 101 to 104 executed in the second position of the C-arm are again executed in the second position of the C-arm, as illustrated by the blocks 201 to 204. This again yields a straight line through the focal point of the X-ray apparatus in the second position of the C-arm and through the image point in the second X-ray image for which the associated object point is to be determined. For this purpose the image point in the first and in the second X-ray image should belong to the same object point as well as possible.

The user can be assisted in choosing the image points in two different X-ray images. After determination of the first image point in the first X-ray image, the connecting line between the first image point and the first focal point can be determined. This connecting line can be projected onto the second X-ray image, yielding the information that the second image point (in the second X-ray image) must be situated on this projected line in the second X-ray image. When the user chooses an image point on this projected line, the connecting line between the selected second image point and the second focal point can be determined and projected onto the first X-ray image again. The user can thus iteratively vary the position of the selected image points in the two X-ray images until adequate accuracy has been achieved.

Finally, in block 105 the position of the object point searched is found by calculation of the point of intersection of the two straight lines yielded by the calculation in the blocks 104 and 204. The exact position of the object point in the object co-ordinate system, imaged as image point in two X-ray images, is then known. This can be used, for example to locate a point, imaged in one or two X-ray images, in the patient, for example by means of a treatment instrument provided with light emitting diodes.

The two straight lines need not necessarily intersect in the three-dimensional space. If there is no point of intersection, the object point searched will be situated at the center of the shortest connecting line between the two straight lines.

Figure 2:
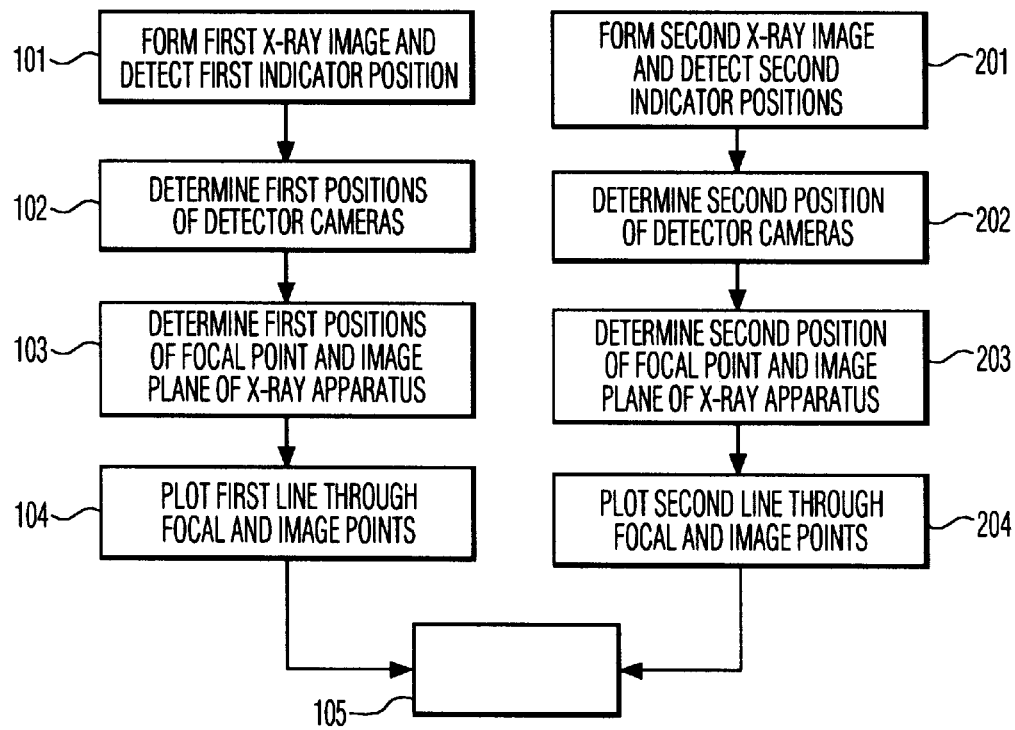
FIG. 2 shows a flow chart of the method according to the invention, FIG. 3 diagrammatically illustrates the position detection by means of the method according to the invention.
Figure 3:
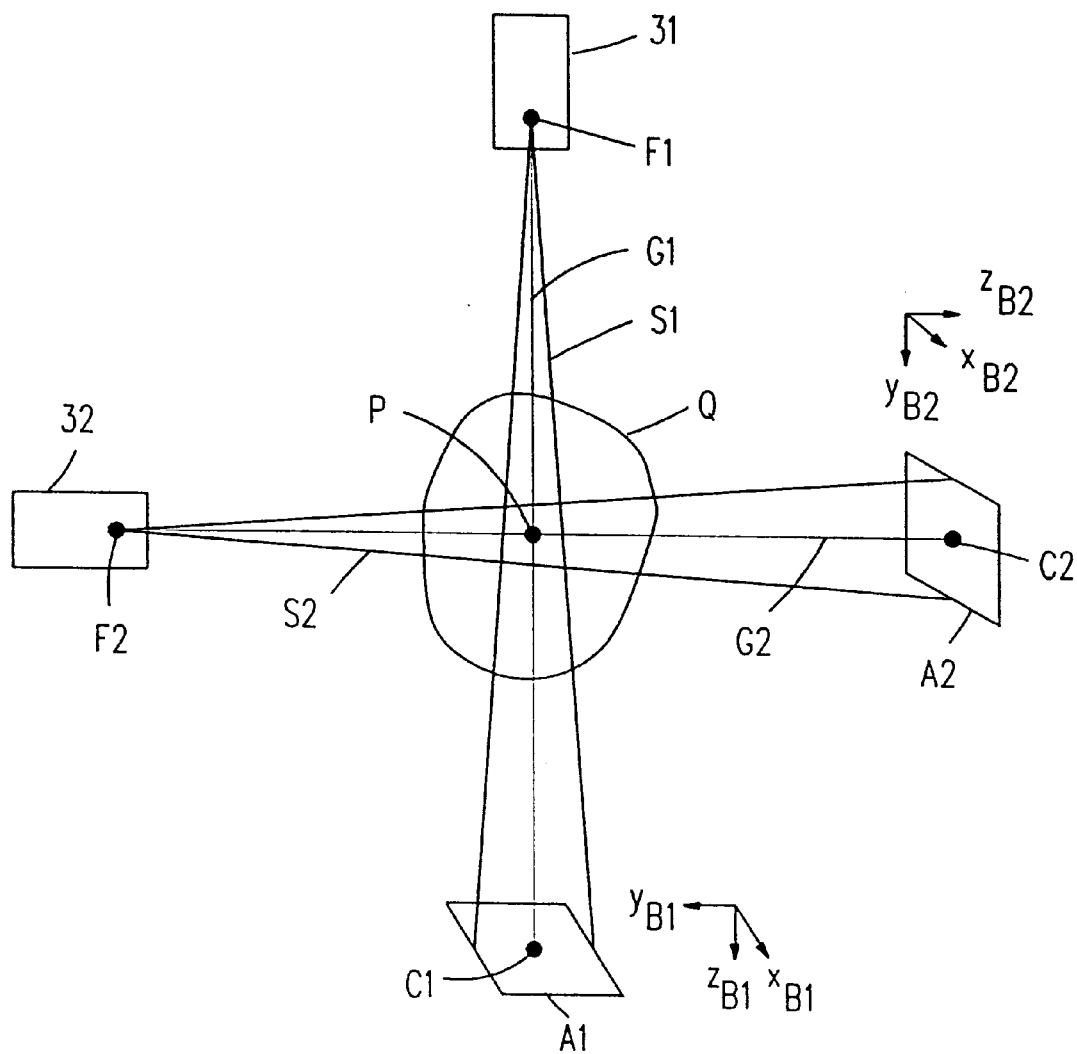

The method shown in FIG. 2 will be illustrated again in FIG. 3. The reference Q denotes a part of an object to be examined whereas the letter P denotes the object point searched. The object Q to be examined is irradiated by a first radiation beam SI in a first position of the X-ray source 31. The radiation S1 emanates from the focal point F1 of the X-ray source 31 and the X-ray image is imaged in the imaging plane A1. The object point P is then imaged, for example as the image point C1 whose co-ordinates in the image co-ordinate system of the first X-ray image (co-ordinate axes $X_{B1}, y_{B1}, z_{B1}$) are known. In a second position of the X-ray source 32, a further X-ray image is formed which is imaged in the imaging plane A2. The object point P is then imaged as the image point C2 in the second image co-ordinate system (co-ordinate axes $x_{B2}, y_{B2}, z_{B2}$)

In conformity with this method, a respective straight line is plotted through the points F1 and C1 (line G1) and F2 and C2 (line G2) and their point of intersection is calculated. This point of intersection is the object point P searched which is imaged in the two X-ray images as the image point C1 and C2, respectively, and whose position in object co-ordinates is now known.

As can be readily seen from FIG. 3, the two X-ray images need not necessarily be formed from mutually perpendicular directions. Moreover, more than two X-ray images can be used for position detection.

Figure 4:
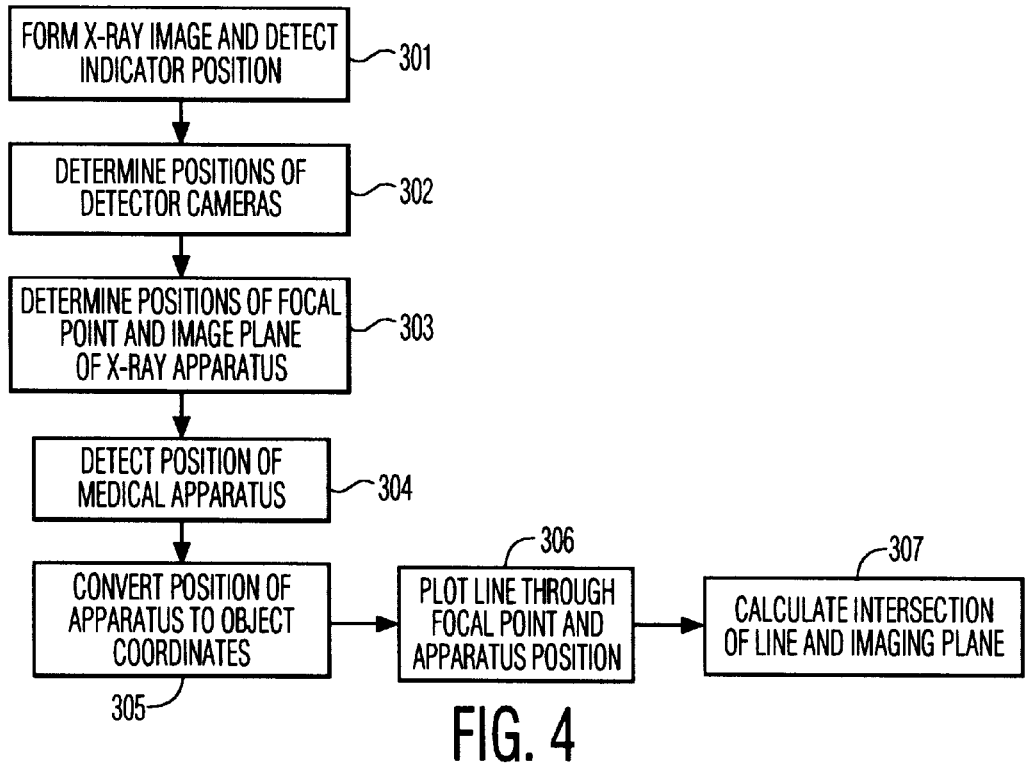
FIG. 4 shows a further flow chart illustrating a version of the method according to the invention.

A further possible application of the method according to the invention will be illustrated on the basis of the flow chart of FIG. 4. This application consists in the determination of the position of a medical apparatus in order to reproduce it, for example in an X-ray image.

The steps which are symbolically represented by the blocks 301 to 303 correspond to the steps represented by the blocks 101 to 103 in FIG. 2, i.e. an X-ray image is formed and the position of the focal spot and the imaging plane of the X-ray apparatus are determined in object co-ordinates. In block 304 the position of an interventional medical apparatus, for example a treatment instrument 12 or a radiation therapy apparatus 13 (see FIG. 1), in the detector co-ordinate system D is detected by the cameras 8, 9. During this detection either the position of the X-ray apparatus must be the same as that in which the X-ray image was formed, or the first position must be stored. The step performed in block 304 may also be performed simultaneously with the steps of the blocks 301 to 303. The detector co-ordinates of the interventional medical apparatus are subsequently converted into object co-ordinates in block 305. In order to determine the position of the apparatus in image co-ordinates and to reproduce this position in the X-ray image, in block 306 first a straight line is plotted through the focal point of the X-ray source and the position of the apparatus in the object co-ordinate system, said line intersecting the imaging plane. In block 307 this point of intersection is calculated, yielding the position of the apparatus in the image co-ordinate system of the X-ray image.

If the position of the X-ray source during the detection of the position of the medical apparatus was not the same as the position during the formation of the X-ray image, the position of the medical apparatus can be converted, using the stored position of the X-ray apparatus, from object co-ordinates into detector co-ordinates of the X-ray apparatus during the X-ray imaging. On the basis thereof the position of the apparatus in the image co-ordinate system of the X-ray image can be determined as described above.

The method of FIG. 4 is used, for example to indicate the position of a surgical instrument, guided within the patient and not being visible from the outside except for its light emitting diode device, in the X-ray image or to reproduce the instrument itself therein. This can be performed while the X-ray apparatus is switched off, provided that the X-ray images have been formed in advance, as well as in the case of a switched-on X-ray apparatus with continuous X-ray exposure, for example when a biopsy needle guided within the body is not visible in the X-ray image.

The position of the instrument can also be continuously updated by continuously repeating the steps described for the blocks 304 to 307.

In case the position of a radiation therapy apparatus is continuously determined by means of the position measuring system, it can be used to aim the therapy beam exactly at a predetermined location which is selected, for example on the basis of an X-ray image.

In order to determine the position of the focal spot and the position of the imaging plane in the detector co-ordinate system, a calibration is required once for an X-ray apparatus, for example upon installation of a position measuring system of the described kind. To this end, a calibration phantom is introduced, quasi as an object to be examined, into the field of view of the cameras and the exposure field of the X-ray apparatus. The calibration phantom is provided with a first indicator device which absorbs X-rays and with a second indicator device for the cameras, for example infrared light-emitting diodes when infrared cameras are used. The position of the two indicator devices relative to one another is then known. Subsequently, an X-ray image of the calibration phantom, in which the first indicator device is also reproduced, is formed by means of the X-ray apparatus and at the same time the position of the second indicator device is detected by means of the cameras. The position of the second indicator device (the light emitting diodes) in detector co-ordinates is then known directly; the position of the first indicator device in detector co-ordinates can be very simply calculated therefrom, because the position of the two indicator devices relative to one another is known. When a suitable calibration phantom and appropriately arranged indicator devices are chosen, the position of the focal point of the X-ray apparatus and the position of the imaging plane of the X-ray apparatus can be very simply derived, on the basis of geometrical considerations, from the known position of the first indicator device and its reproduction in the X-ray image. In as far as the arrangement of the cameras on the X-ray apparatus is not changed at a later stage, these values remain the same quasi as fixed values for the X-ray apparatus and can be assumed to be known and used for the method according to the invention.

In order to enhance the accuracy of the position detection even further, or in case the lines of sight of the camera are liable to be obscured, additionally a further detector device which is mounted, for example on a stand as in the known case, can be used.

The method and the device according to the invention can also be used for diagnostic purposes. For example, positionally correct combination of a plurality of X-ray images, formed in different positions of the X-ray table, can be performed so as to form a single X-ray image. To this end, for example the focus and the imaging plane are kept stationary and the patient table is moved, a respective X-ray image being formed in two different positions of the patient table. The position of the patient table can then be determined via the indicator device attached to the patient table or to the patient.

The invention is not restricted to the application involving a C-arm X-ray apparatus as shown in the drawings. X-ray images from different positions relative to an object to be examined can also be acquired by means of other X-ray apparatus, for example comprising a pivotable patient table and a stationary X-ray source and image pick-up device. In X-ray apparatus of this kind, for example the cameras could be mounted on the X-ray source and the light-emitting diodes on the pivotable table.

All references cited herein are incorporated herein by reference in their entirety and for all purposes to the same extent as if each individual publication or patent or patent application was specifically and individually indicated to be incorporated by reference in its entirety for all purposes.

We claim:

1. A method of position detection in X-ray imaging, in which
    at least one X-ray image of an object to be examined is formed by means of an X-ray apparatus and the position of an indicator device, provided so as to be stationary relative to the object to be examined, in a detector co-ordinate system coupled to the detector device is determined by means of a detector device mounted on the X-ray apparatus,
    the position of the X-ray apparatus is determined in an object co-ordinate system, which is coupled to the object to be examined, and subsequently the position of an object point which is imaged, as an image point in an X-ray image, is determined in the object co-ordinate system.

2. A method as claimed in claim 1, characterized in that at least two X-ray images of the object to be examined are formed from different directions, the position of the focal point and the position of the imaging plane of the X-ray apparatus in the object coordinate system being determined simultaneously with the X-ray image acquisition.

3. A method as claimed in claim 2, characterized in that the position of the object point is determined by means of two straight lines, the first straight line extending through the image point associated with the object point in a first X-ray image and through the first position of the focal point, whereas the second straight line extends through the image point associated with the object point in a second X-ray image and through the second position of the focal point, the object point being the point of intersection of the two straight lines or the central point of the shortest connecting line between the two straight lines.

4. A method as claimed in claim 3, characterized in that the detector device detects the position of a medical apparatus, provided with a further indicator device, in the detector co-ordinate system, the position of the medical apparatus in the image coordinate system of an X-ray image being determined from its position in the detector co-ordinate system.

5. A method as claimed in claim 4, characterized in that the position of the medical apparatus in the image co-ordinate system is calculated from the point of intersection between the imaging plane and a straight line which extends through the focal point and the position of the medical apparatus in the object co-ordinate system.

6. A method as claimed in claim 2, characterized in that the detector device detects the position of a medical apparatus, provided with a further indicator device, in the detector co-ordinate system, the position of the medical apparatus in the image coordinate system of an X-ray image being determined from its position in the detector co-ordinate system.

7. A method as claimed in claim 6, characterized in that the position of the medical apparatus in the image co-ordinate system is calculated from the point of intersection between the imaging plane and a straight line which extends through the focal point and the position of the medical apparatus in the object co-ordinate system.

8. A method as claimed in claim 1, characterized in that the detector device detects the position of a medical apparatus, provided with a further indicator device, in the detector co-ordinate system, the position of the medical apparatus in the image co-ordinate system of an X-ray image being determined from its position in the detector co-ordinate system.

9. A method as claimed in claim 8, characterized in that the position of the medical apparatus in the image co-ordinate system is calculated from the point of intersection between the imaging plane and a straight line which extends through the focal point and the position of the medical apparatus in the object co-ordinate system.

10. A device for X-ray imaging, including an X-ray apparatus, a detector device mounted on the X-ray apparatus with at least two detector elements and an indicator device which is provided so as to be stationary relative to an object to be examined, and control and processing means configured for determining the position of the X-ray apparatus in an object co-ordinate system, which is coupled to the object to be examined, and for determining subsequently the position in the object co-ordinate system of an object point which is imaged as an image point in an X-ray image.

11. A device as claimed in claim 10, characterized in that the detector device is mounted on the X-ray source or on the X-ray image pick-up or X-ray image intensifier device.

12. A device as claimed in claim 11, characterized in that a further indicator device is mounted on a treatment instrument or a radiation therapy device.

13. A device as claimed in claim 12, characterized in that the indicator devices include optical light source markers, for example light emitting diodes which emit infrared light or visible light, retro-reflective markers or markers provided with a recognition pattern.

14. A device as claimed in claim 11, characterized in that the indicator devices include optical light source markers, for example light emitting diodes which emit infrared light or visible light, retro-reflective markers or markers provided with a recognition pattern.

15. A device as claimed in claim 10, characterized in that a further indicator device is mounted on a treatment instrument or a radiation therapy device.

16. A device as claimed in claim 15, characterized in that the indicator devices include optical light source markers, for example light emitting diodes which emit infrared light or visible light, retro-reflective markers or markers provided with a recognition pattern.

17. A device as claimed in claim 10, characterized in that the indicator devices include optical light source markers, for example light emitting diodes which emit infrared light or visible light, retro-reflective markers or markers provided with a recognition pattern.

18. A device as claimed in claim 10, characterized in that the detector device includes two optical detectors, detecting a respective two-dimensional position, or three optical detectors, each of which detects a respective one-dimensional position, said detectors being capable of detecting infrared light or visible light and preferably being infrared CCD cameras, each of the indicator devices including at least three light emitting diodes emitting infrared light or visible light.

19. A device as claimed in claim 10, characterized in that the indicator device includes at least one electromagnetic transmitter device, the detector device including at least one electromagnetic receiver device.

20. A device as claimed in claim 10, characterized in that the X-ray apparatus is a C-arm X-ray apparatus.

* * * * *